(12) United States Patent
Bethke

(10) Patent No.: US 12,241,117 B2
(45) Date of Patent: *Mar. 4, 2025

(54) METHODS FOR CHARACTERIZING COPY NUMBER VARIATION USING PROXIMITY-LITIGATION SEQUENCING

(71) Applicant: Natera, Inc., San Carlos, CA (US)

(72) Inventor: Axel Bethke, Belmont, CA (US)

(73) Assignee: Natera, Inc., San Carlos, CA (US)

( * ) Notice: Subject to any disclaimer, the term of this patent is extended or adjusted under 35 U.S.C. 154(b) by 102 days.

This patent is subject to a terminal disclaimer.

(21) Appl. No.: 17/977,208

(22) Filed: Oct. 31, 2022

(65) Prior Publication Data

US 2023/0060579 A1 Mar. 2, 2023

Related U.S. Application Data

(63) Continuation of application No. 16/338,110, filed as application No. PCT/US2017/054870 on Oct. 3, 2017, now Pat. No. 11,485,996.

(60) Provisional application No. 62/404,176, filed on Oct. 4, 2016.

(51) Int. Cl.
*C12Q 1/68* (2018.01)
*C12Q 1/6827* (2018.01)

(52) U.S. Cl.
CPC ................... *C12Q 1/6827* (2013.01)

(58) Field of Classification Search
None
See application file for complete search history.

(56) References Cited

U.S. PATENT DOCUMENTS

| 2016/0239602 | A1* | 8/2016 | Shendure | ............... G16B 30/00 |
| 2017/0314014 | A1 | 11/2017 | Green et al. | |
| 2017/0362649 | A1* | 12/2017 | Lieberman-Aiden | ...................... C12Q 1/6869 |
| 2018/0187241 | A1 | 7/2018 | Selvaraj et al. | |
| 2020/0024653 | A1 | 1/2020 | Bethke | |

FOREIGN PATENT DOCUMENTS

| WO | 2013/078470 A2 | 5/2013 |
| WO | 2017/058784 A1 | 4/2017 |

* cited by examiner

*Primary Examiner* — Aaron A Priest

(57) ABSTRACT

Disclosed here is a method for detecting genome rearrangement in a biological sample, comprising: obtaining a contact matrix plotted from proximity ligation sequencing data of at least one chromosome; identifying an abnormal contact pattern in the contact matrix compared to the contact matrix of a reference genome; comparing the abnormal contact pattern in the contact matrix to one or more known patterns associated with genomic rearrangement to identify a type of genomic rearrangement causing the abnormal contact pattern. Also disclosed is a method for detecting genome rearrangement in a biological sample, comprising: selecting linked chromosomal fragments from proximity ligation sequencing data of at least one chromosome, identifying an abnormal covalent bonding pattern of the linked chromosomal fragments compared to a reference genome; and comparing the abnormal covalent bonding pattern to one or more known patterns associated with genomic rearrangement to identify genomic rearrangement causing the abnormal covalent bonding pattern.

18 Claims, 8 Drawing Sheets

METHODS FOR CHARACTERIZING COPY NUMBER VARIATION USING PROXIMITY-LITIGATION SEQUENCING

CROSS-REFERENCE TO RELATED APPLICATIONS

This application is a continuation of U.S. application Ser. No. 16/338,110, filed on Mar. 29, 2019, which is a U.S. National Stage Application of PCT/US2017/054870, filed Oct. 3, 2017, which claims the benefit of U.S. Provisional Application Ser. No. 62/404,176, filed Oct. 4, 2016, which is hereby incorporated by reference in its entirety.

BACKGROUND

Copy number variations are structural variations in the human genome that play an important role in the development of various diseases and genetic disorders. Copy number variation may be caused by different types of chromosomal rearrangement events, such as deletion, duplication, and relocation of DNA fragments within a chromosome. Copy number variation has been associated with various forms of cancer and neurological disorders. Detection of copy number variants of a chromosome of interest or a portion thereof in a biopsy sample of a patient can be a powerful tool to identify genetic diagnostic or prognostic indicators of a disease or disorder. Detection of copy number variation is also useful in detecting genetic disorders in non-invasive prenatal testing. The structure of rearrangements is unique to each patient and defining its exact nature is relevant for diagnostics and treatment decisions.

Nuclear proximity ligation assay was first described in Cullen et al., *Science* 261:203-206 (1993). Subsequently, nuclear proximity ligation has been combined with high-throughput sequencing to probe three-dimensional proximity of different genomic segments that are distant from each other on the one-dimensional linear space of the chromosome. For example, ChIA-PET probes chromatin interaction by paired-end tag sequencing to detect genome wide chromatin interactions mediated by specific protein factors, and Hi-C involves high-throughput chromatin conformation capture for mapping large-scale structures such as topologically associated domains. See Selvaraj et al., *Nature Biotechnology* 31:1111-1118 (2013) and Rao et al., *Cell* 159: 1665-1680 (2014).

SUMMARY

The present inventors successfully applied proximity ligation sequencing in the detection of copy number variations that are characterized by various types of chromosomal rearrangement. Accordingly, a first aspect the invention described herein relates to a method for detecting genome rearrangement in a biological sample, comprising: selecting linked chromosomal fragments from proximity ligation sequencing data of at least one chromosome of the biological sample, wherein the selected linked chromosomal fragments substantially originate from covalent bonding of two chromosomal fragments; identifying an abnormal covalent bonding pattern of the linked chromosomal fragments compared to a reference genome; and comparing the abnormal covalent bonding pattern to one or more known patterns associated with genomic rearrangement to identify a type of genomic rearrangement causing the abnormal covalent bonding pattern.

In some embodiments, the genomic rearrangement identified is deletion of chromosomal fragments. In some embodiments, the deletion of a chromosomal fragment is identified by: (i) a loss of covalent bonding between two or more continuous chromosomal fragments that are linked to each other in the reference genome, and (ii) a gain of covalent bonding between two chromosomal fragments that are separated by one or more continuous chromosomal fragments in the reference genome.

In some embodiments, the genomic rearrangement identified is duplication of chromosomal fragments. In some embodiments, the duplication of a chromosomal fragment is identified by: (i) a loss of covalent bonding between a first and second chromosomal fragments that are linked to each other in the reference genome, (ii) a gain of covalent bonding between the first chromosomal fragment and a third chromosomal fragment, wherein the first chromosomal fragment is separated from the third chromosomal fragment in the reference genome by at least one chromosomal fragment; (iii) a gain of covalent bonding between the second chromosomal fragment and a fourth chromosomal fragment, wherein the second chromosomal fragment is separated from the fourth chromosomal fragment in the reference genome by at least one chromosomal fragment; and (iv) an enhancement of covalent bonding between two or more continuous chromosomal fragments, from the third chromosomal fragment to the fourth chromosomal fragment, that are linked to each other in the reference genome.

In some embodiments, the genomic rearrangement identified is relocation of chromosomal fragments. In some embodiments, the relocation of chromosomal fragments is identified by: (i) a loss of covalent bonding between a first and second chromosomal fragments that are linked to each other in the reference genome, (ii) a gain of covalent bonding between the first chromosomal fragment and a third chromosomal fragment, wherein the first chromosomal fragment is separated from the third chromosomal fragment in the reference genome by at least one chromosomal fragment; (iii) a gain of covalent bonding between the second chromosomal fragment and a fourth chromosomal fragment, wherein the second chromosomal fragment is separated from the fourth chromosomal fragment in the reference genome by at least one chromosomal fragment; (iv) a loss of covalent bonding between the third chromosomal fragment and a fifth chromosomal fragments, wherein the third and fifth chromosomal fragments are linked to each other in the reference genome; (v) a loss of covalent bonding between the fourth chromosomal fragment and a sixth chromosomal fragments, wherein the fourth and sixth chromosomal fragments are linked to each other in the reference genome; and (vi) a gain of covalent bonding between the fifth and sixth chromosomal fragments, wherein the fifth chromosomal fragment is separated from the sixth chromosomal fragment in the reference genome by two or more continuous chromosomal fragments, from the third chromosomal fragment to the fourth chromosomal fragment.

A second aspect the invention described herein relates to a method for detecting genome rearrangement in a biological sample, comprising: obtaining a contact matrix plotted from proximity ligation sequencing data of at least one chromosome of the biological sample; identifying an abnormal contact pattern in the contact matrix compared to the contact matrix of a reference genome; and comparing the abnormal contact pattern in the contact matrix to one or more known patterns associated with genomic rearrangement to identify a type of genomic rearrangement causing the abnormal contact pattern.

In some embodiments, the genomic rearrangement identified is deletion of chromosomal fragments. In some embodiments, the deletion of a chromosomal fragment is identified by: (i) a loss of one or more cis interactions between two or more continuous chromosomal fragments that are linked to each other in the reference genome, and (ii) a gain of a trans interaction between two chromosomal fragments that are separated by the two or more continuous chromosomal fragments in the reference genome.

In some embodiments, the genomic rearrangement identified is duplication of chromosomal fragments. In some embodiments, the duplication of a chromosomal fragment is identified by: (i) a loss of a cis interaction between a first and second chromosomal fragments that are linked to each other in the reference genome, (ii) a gain of a trans interaction between the first chromosomal fragment and a third chromosomal fragment, wherein the first chromosomal fragment is separated from the third chromosomal fragment in the reference genome by at least one chromosomal fragment; (iii) a gain of a trans interaction between the second chromosomal fragment and a fourth chromosomal fragment, wherein the second chromosomal fragment is separated from the fourth chromosomal fragment in the reference genome by at least one chromosomal fragment; and (iv) an enhancement of one or more cis interactions between two or more continuous chromosomal fragments, from the third chromosomal fragment to the fourth chromosomal fragment, that are linked to each other in the reference genome.

In some embodiments, the genomic rearrangement identified is relocation of chromosomal fragments. In some embodiments, the relocation of chromosomal fragments is identified by: (i) a loss of a cis interaction between a first and second chromosomal fragments that are linked to each other in the reference genome, (ii) a gain of a trans interaction between the first chromosomal fragment and a third chromosomal fragment, wherein the first chromosomal fragment is separated from the third chromosomal fragment in the reference genome by at least one chromosomal fragment; (iii) a gain of a trans interaction between the second chromosomal fragment and a fourth chromosomal fragment, wherein the second chromosomal fragment is separated from the fourth chromosomal fragment in the reference genome by at least one chromosomal fragment; (iv) a loss of a cis interaction between the third chromosomal fragment and a fifth chromosomal fragments, wherein the third and fifth chromosomal fragments are linked to each other in the reference genome; (v) a loss of a cis interaction between the fourth chromosomal fragment and a sixth chromosomal fragments, wherein the fourth and sixth chromosomal fragments are linked to each other in the reference genome; and (vi) a gain of a trans interaction between the fifth and sixth chromosomal fragments, wherein the fifth chromosomal fragment is separated from the sixth chromosomal fragment in the reference genome by two or more continuous chromosomal fragments, from the third chromosomal fragment to the fourth chromosomal fragment.

A third aspect the invention described herein relates to a method for detecting genome rearrangement in a biological sample, comprising: subjecting the biological sample to proximity ligation sequencing to obtain proximity ligation sequencing data of at least one chromosome of the biological sample; selecting linked chromosomal fragments from the proximity ligation sequencing data, wherein the selected linked chromosomal fragments substantially originate from covalent bonding of two chromosomal fragments; identifying an abnormal covalent bonding pattern of the linked chromosomal fragments compared to a reference genome; and comparing the abnormal covalent bonding pattern to one or more known patterns associated with genomic rearrangement to identify a type of genomic rearrangement causing the abnormal covalent bonding pattern.

A fourth aspect the invention described herein relates to a method for detecting genome rearrangement in a biological sample, comprising: subjecting the biological sample to proximity ligation sequencing to obtain proximity ligation sequencing data of at least one chromosome of the biological sample; obtaining a contact matrix plotted from the proximity ligation sequencing data; identifying an abnormal contact pattern in the contact matrix compared to the contact matrix of a reference genome; comparing the abnormal contact pattern in the contact matrix to one or more known patterns associated with genomic rearrangement to identify a type of genomic rearrangement causing the abnormal contact pattern.

A fifth aspect the invention described herein relates to a method for diagnosing a disease or genetic disorder associated with copy number variation, comprising: subjecting a tissue biopsy sample of a patient to proximity ligation sequencing to obtain proximity ligation sequencing data of at least one chromosome of the tissue biopsy sample of the patient; selecting linked chromosomal fragments from the proximity ligation sequencing data, wherein the selected linked chromosomal fragments substantially originate from covalent bonding of two chromosomal fragments; identifying an abnormal covalent bonding pattern of the linked chromosomal fragments compared to a reference genome; comparing the abnormal covalent bonding pattern to one or more known patterns associated with copy number variation to identify a type of copy number variation causing the abnormal covalent bonding pattern and the location and/or length of the copy number variation, wherein the copy number variation identified is correlated to a disease or genetic disorder.

A sixth aspect the invention described herein relates to a method for diagnosing a disease or genetic disorder associated with copy number variation, comprising: subjecting a tissue biopsy sample of a patient to proximity ligation sequencing to obtain proximity ligation sequencing data of at least one chromosome of the tissue biopsy sample of the patient; obtaining a contact matrix plotted from the proximity ligation sequencing data; identifying an abnormal contact pattern in the contact matrix compared to the contact matrix of a reference genome; and comparing the abnormal contact pattern in the contact matrix to one or more known patterns associated with copy number variation to identify a type of copy number variation causing the abnormal contact pattern and the location and/or length of the copy number variation; wherein the copy number variation identified is correlated to a disease or genetic disorder.

An addition aspect of the invention described herein relates to use of proximity ligation sequencing data to reconstruct one-dimensional genome structure (linear sequence) of a genome that has experienced chromosomal rearrangements.

These and other features, together with the organization and manner of operation thereof, will become apparent from the following detailed description when taken in conjunction with the accompanying drawings.

DETAILED DESCRIPTION

Figure 1:
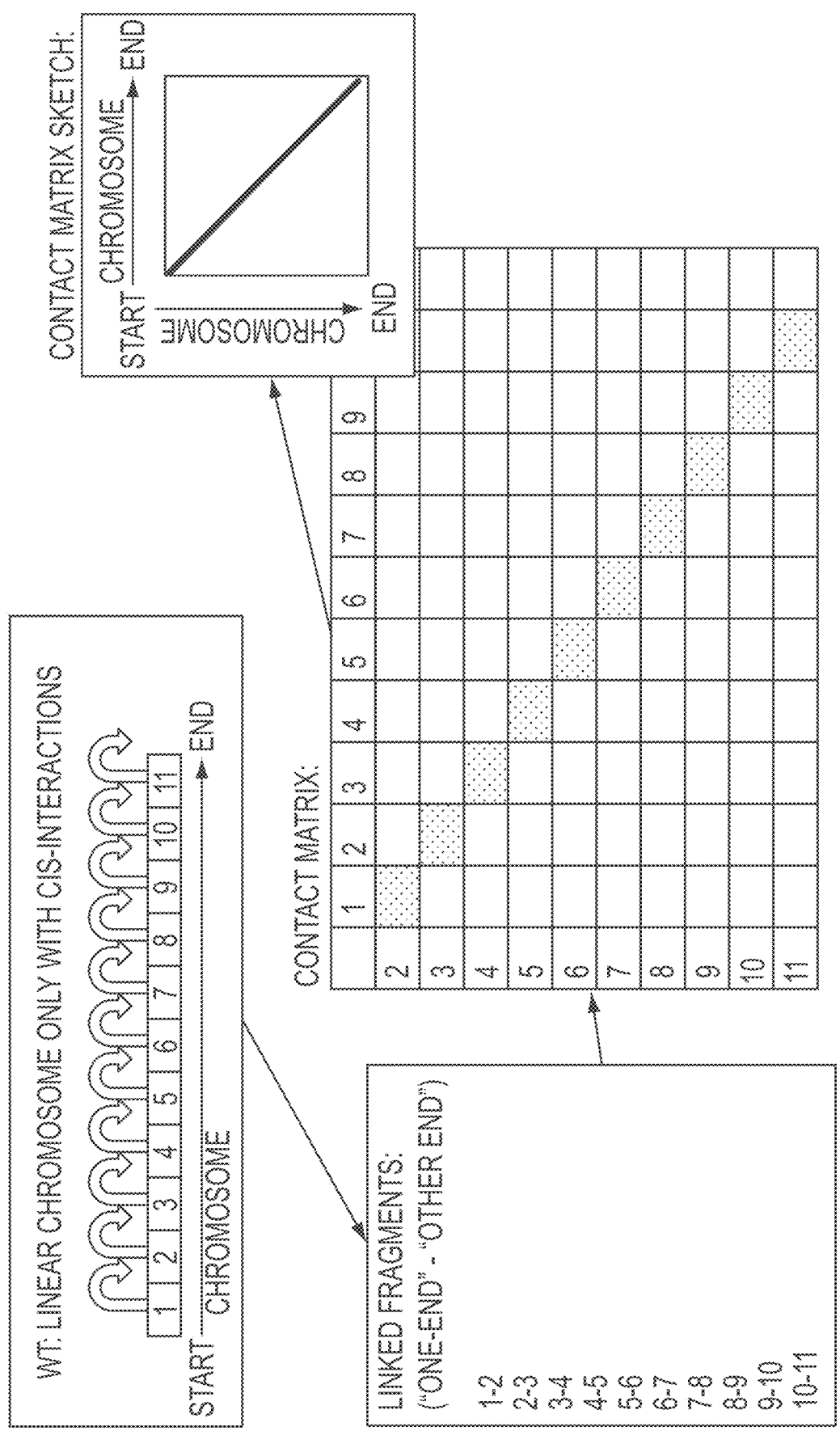
FIG. 1: PL-Seq results of a continuous chromosome plotted as contact matrix. The closer two sequences on the same chromosome are to each other, the more contacts are detected. Most of the interactions are cis-interactions within the same chromosome. A linear chromosome with only cis-interactions will plot in a contact matrix in a continuous pattern.

Reference will now be made in detail to some specific embodiments of the invention contemplated by the inventors for carrying out the invention. Certain examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details.

Various techniques and mechanisms of the present invention will sometimes be described in singular form for clarity. However, it should be noted that some embodiments include multiple iterations of a technique or multiple instantiations of a mechanism unless noted otherwise.

Methods for Identifying Genome Rearrangement and Copy Number Variation

The invention described herein encompasses a method for detecting genome rearrangement and copy number variation in a biological sample using proximity ligation sequencing data.

In some embodiments, the method comprises subjecting a biological sample to proximity ligation sequencing to obtain proximity ligation sequencing data of at least one chromosome of the biological sample. The proximity ligation sequencing data can be obtained from, for example, a biological sample of a mammal. The proximity ligation sequencing data can be obtained from, for example, a biological sample of a human subject. The proximity ligation sequencing data can be obtained from, for example, a tissue biopsy sample of a human subject.

Specific biological samples include tissue biopsies such as tumors tissues and placenta tissues (NIPT), captured single cells such as nucleated fetal red blood cells in pregnant women's blood (NIPT), circulating tumor cells and circulating immune cells (e.g., to screen for VDJ recombination in T- and B-cells), as well as cell culture samples (e.g., to monitor genome integrity of the culture such as stem cell expansion).

Certain embodiments of proximity ligation sequencing are described in Selvaraj et al., *Nature Biotechnology* 31:1111-1118 (2013) and Rao et al., *Cell* 159:1665-1680 (2014), which are incorporated by reference in their entireties. For example, the proximity ligation sequencing can comprise crosslinking genomic DNAs in situ. The crosslinked DNA can be digested with a restriction enzyme and ligated to form linked fragments. The linked fragments can be isolated from cells and sequenced to obtain proximity ligation sequencing data. The proximity ligation sequencing data of a chromosome can be plotted into a contact matrix showing both locations of contacts and contact frequencies thereof.

FIG. 1 shows a continuous chromosome plotted as a contact matrix, with chromosomal fragments divided into consecutively numbered blocks, and contacts between chromosomal fragments highlighted in the contact matrix as pixels. Typically, the closer two fragments on the same chromosome are to each other, the more contacts are detected. Most of the interactions are cis-interactions within the same chromosome. A linear chromosome with only cis-interactions will plot in a contact matrix in a continuous pattern.

Known contact matrix plotted from proximity ligation sequencing data, however, include many pixels that originate not from covalent bonding between two chromosomal fragments, but from noncovalent interactions between two distant chromosomal fragments. The contact frequencies of these pixels/blocks are typically lower than the contact frequencies of those correlating to covalently bonded chromosomal fragments. Accordingly, in some embodiments, the pixels and sequencing reads correlating to noncovalent interactions between two distant chromosomal fragments are filtered and separated from the pixels and sequencing reads correlating to covalently bonded chromosomal fragments, prior to analyzing the pixels and sequencing reads for detection of genome rearrangement and copy number variation.

The genome rearrangement and copy number variation can be detected by directly analyzing the sequencing reads of proximity ligation sequencing. The method can comprise the steps of: selecting linked chromosomal fragments from proximity ligation sequencing data of at least one chromosome of the biological sample, wherein the selected linked chromosomal fragments substantially originate from covalent bonding of two chromosomal fragments; identifying an abnormal covalent bonding pattern of the linked chromosomal fragments compared to a reference genome; and comparing the abnormal covalent bonding pattern to one or more known patterns associated with genomic rearrangement to identify a genomic rearrangement causing the abnormal covalent bonding pattern. A reference genome can refer to a genome before the occurrence of one or more rounds of rearrangement, whereas a sample tested may comprise one or more rounds of rearrangement.

In some embodiments, a linked-fragments threshold count can be defined, wherein linked-fragments with counts below the threshold are considered as transient interactions resulting from protein-DNA interactions that are disregarded, and linked-fragments with counts above the threshold are considered as permanent DNA-DNA bonds. Next, the linked fragments that originate from newly formed DNA-DNA covalent bonds (rearrangement) can be listed, and rearrangement patterns causative to such linked fragments can be identified.

The genome rearrangement and copy number variation can also be detected by analyzing the contact matrix plotted from proximity ligation sequencing data. The method can comprise the steps of: obtaining a contact matrix plotted from proximity ligation sequencing data of at least one chromosome of the biological sample; identifying an abnormal contact pattern in the contact matrix compared to the contact matrix of a reference genome; and comparing the abnormal contact pattern in the contact matrix to one or more known patterns associated with genomic rearrangement to identify a genomic rearrangement causing the abnormal contact pattern.

In some embodiments, abnormal contact matrix patterns are recorded. The recorded patterns are compared to known patterns of specific rearrangements. Recognition of a specific pattern identifies the type of the rearrangement(s). The exact location of each recognized abnormal pattern allows identification of exact locations of the observed rearrangement.

The identification of the type, location, length, and/or orientation of the genome arrangement are described in detail in the following paragraphs.

Deletion of Chromosomal Fragments within a Genome

In some embodiments, the method described herein can be used to detect deletion of chromosomal fragments.

Figure 2:
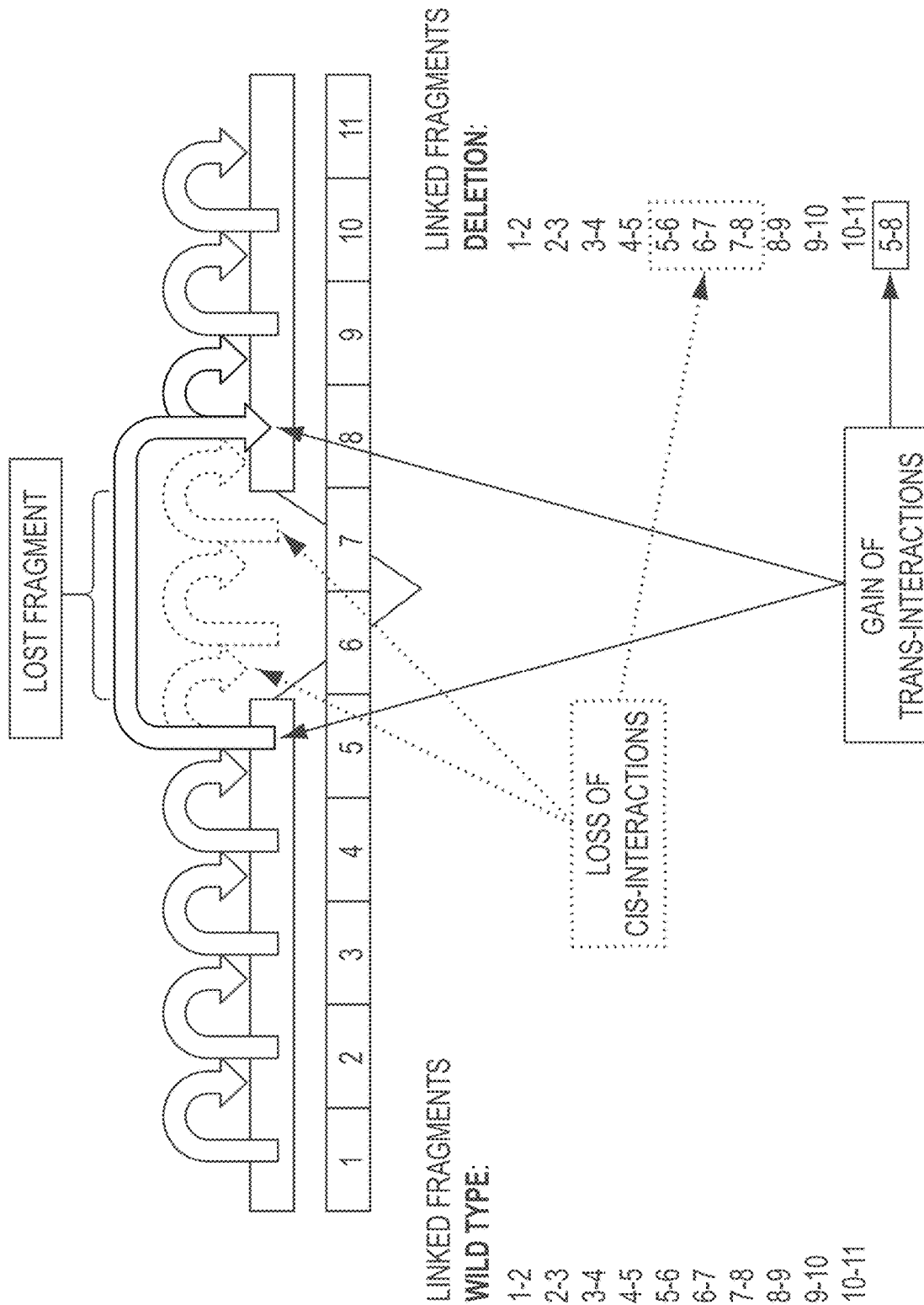
FIG. 2: Deletion of a fragment within a chromosome. A deletion generates one new trans-interaction at reconnection of 5' and 3' donor location that reveals location of start/end points of the deletion. All cis-interactions within deleted fragment are lost, which reveals deletion length. Chromosome sequences are divided into consecutively numbered blocks. Block arrows indicate cis- and trans-interactions between sequences blocks, represented by numbered blocks. Lists show linked fragments as block numbers for both interacting sequences separated by a dash. Shown are lists for linked fragments of a wild type chromosome as reference and for the corresponding rearranged chromosome. Thin arrows point at interactions that appear or disappear due to genome rearrangements of various kinds, and connect to the corresponding linked fragments.
Figure 3:
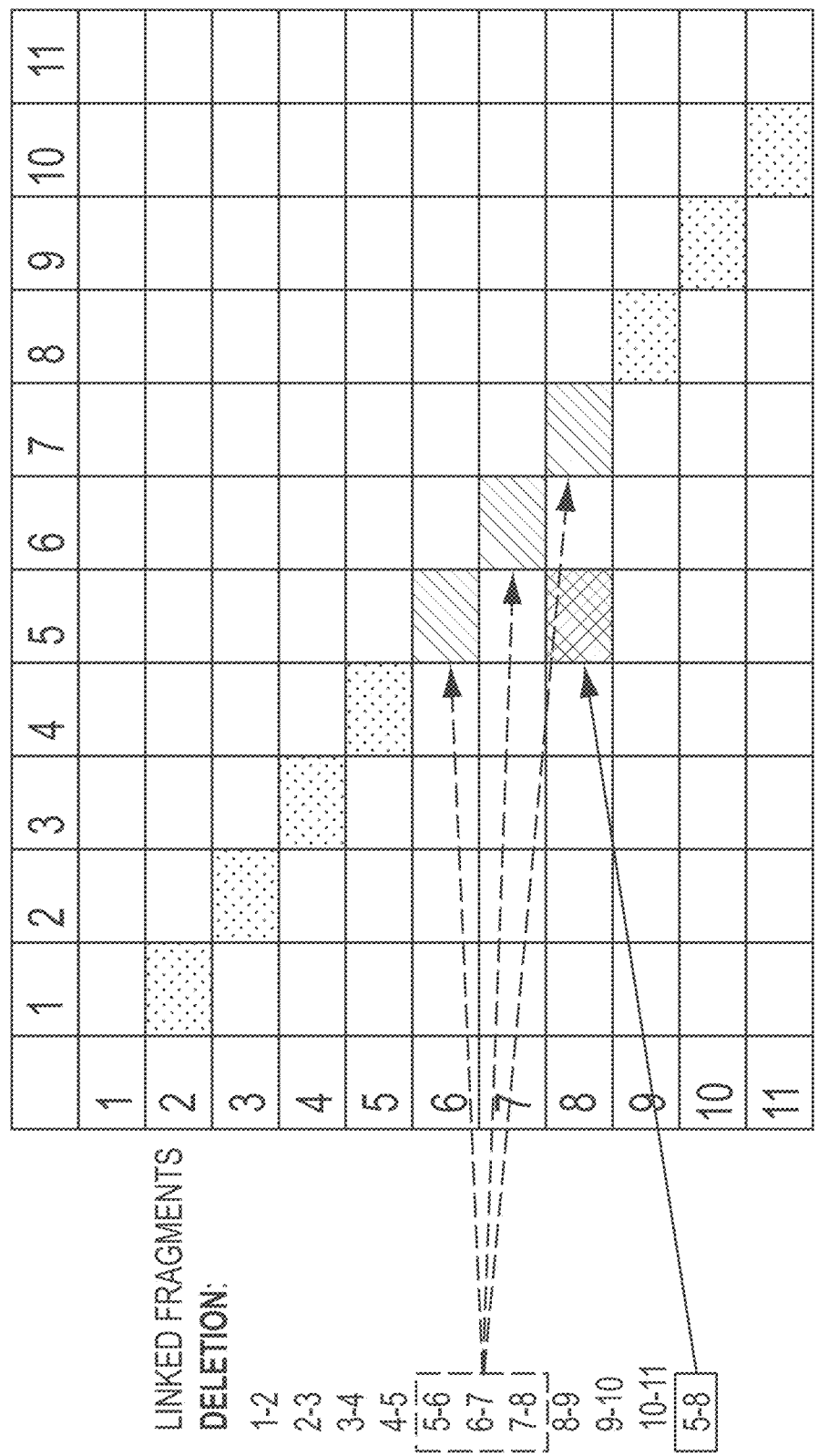
FIG. 3: Contact matrix corresponding to the deletion of a chromosomal fragment as shown in FIG. 2.

As shown in FIGS. 2 and 3, a deletion of a fragment within a chromosome can generate a new trans-interaction at reconnection of 5' and 3' donor location that reveals location of start/end points of the deletion. All cis-interactions within the deleted fragment are lost, which reveals deletion length.

Accordingly, in some embodiments wherein sequencing reads of proximity ligation sequencing are directly used to analyze genome rearrangement and copy number variation, the deletion of a chromosomal fragment can be identified by one or more of: (i) a loss of covalent bonding between two or more continuous chromosomal fragments that are linked to each other in the reference genome (e.g., loss of contact between 5 and 6, 6 and 7, and 7 and 8 in FIG. 2), and (ii) a gain of covalent bonding between two chromosomal fragments that are separated by one or more continuous chromosomal fragments in the reference genome (e.g., gain of contact between 5 and 8 in FIG. 2).

In other embodiments wherein a contact matrix is plotted from proximity ligation sequencing data and used to analyze genome rearrangement and copy number variation, the deletion of a chromosomal fragment can be identified by one or more of: (i) a loss of one or more cis interactions between two or more continuous chromosomal fragments that are linked to each other in the reference genome (e.g., loss of contact between 5 and 6, 6 and 7, and 7 and 8 in FIG. 3), and (ii) a gain of a trans interaction between two chromosomal fragments that are separated by the two or more continuous chromosomal fragments in the reference genome (e.g., gain of contact between 5 and 8 in FIG. 3).

Duplication of Chromosomal Fragments within a Genome

In some embodiments, the method described herein can be used to detect duplication (i.e., amplification and insertion) of chromosomal fragments.

Figure 4:
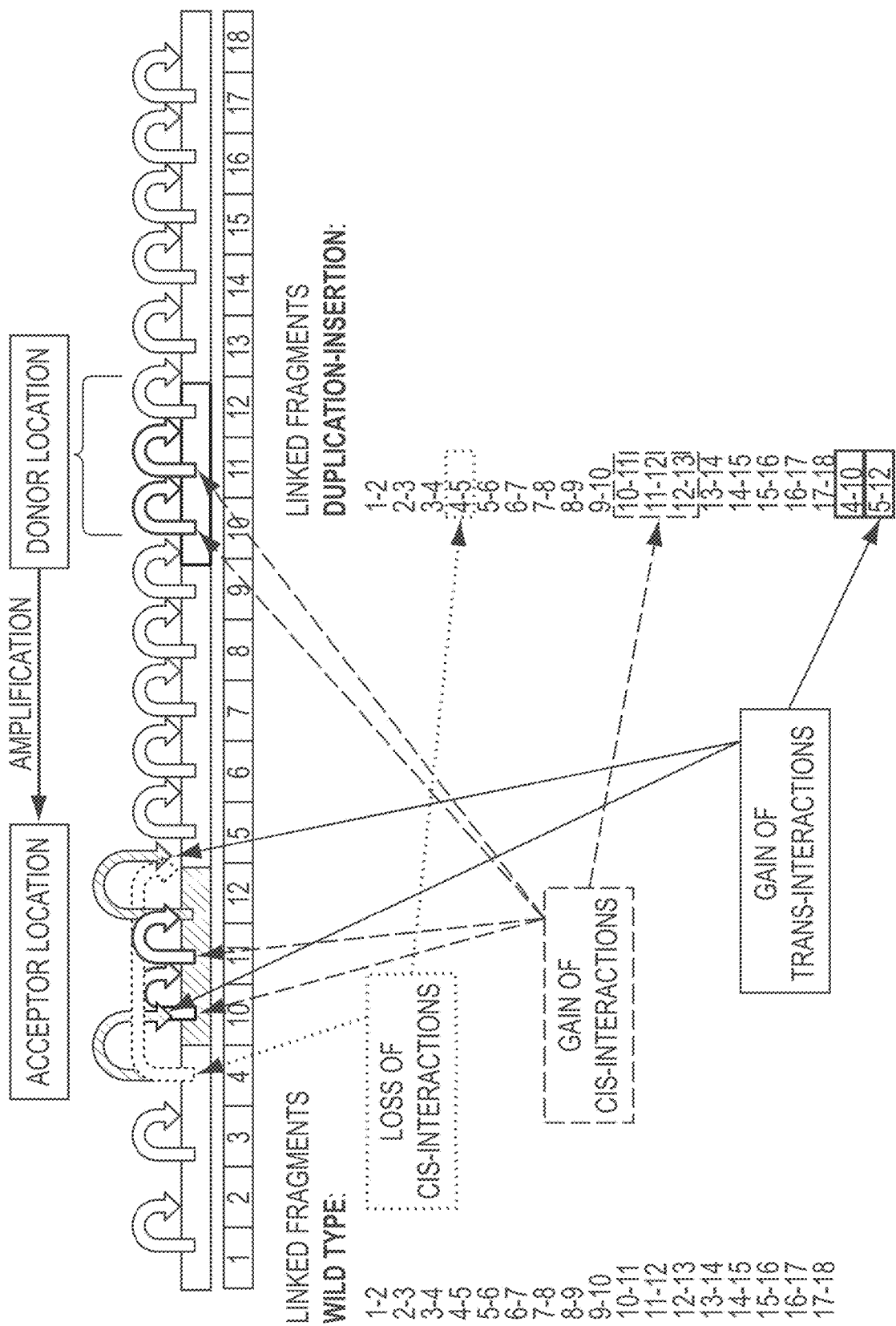
FIG. 4: Amplification and insertion of a fragment within a chromosome. An amplification-insertion generates two new trans-interaction located at 5' donor and 5' acceptor location and at 3' donor and 3' acceptor location that reveal length and orientation of the duplication. All cis-interactions within the duplicated fragment are duplicated and quantification reveals fold amplification of duplication. One single cis-interaction at insertion location is lost which reveals insertion location. Chromosome sequences are divided into consecutively numbered blocks. Block arrows indicate cis- and trans-interactions between sequences blocks, represented by numbered blocks. Lists show linked fragments as block numbers for both interacting sequences separated by a dash. Shown are lists for linked fragments of a wild type chromosome as reference and for the corresponding rearranged chromosome. Thin arrows point at interactions that appear or disappear due to genome rearrangements of various kinds, and connect to the corresponding linked fragments.
Figure 5:
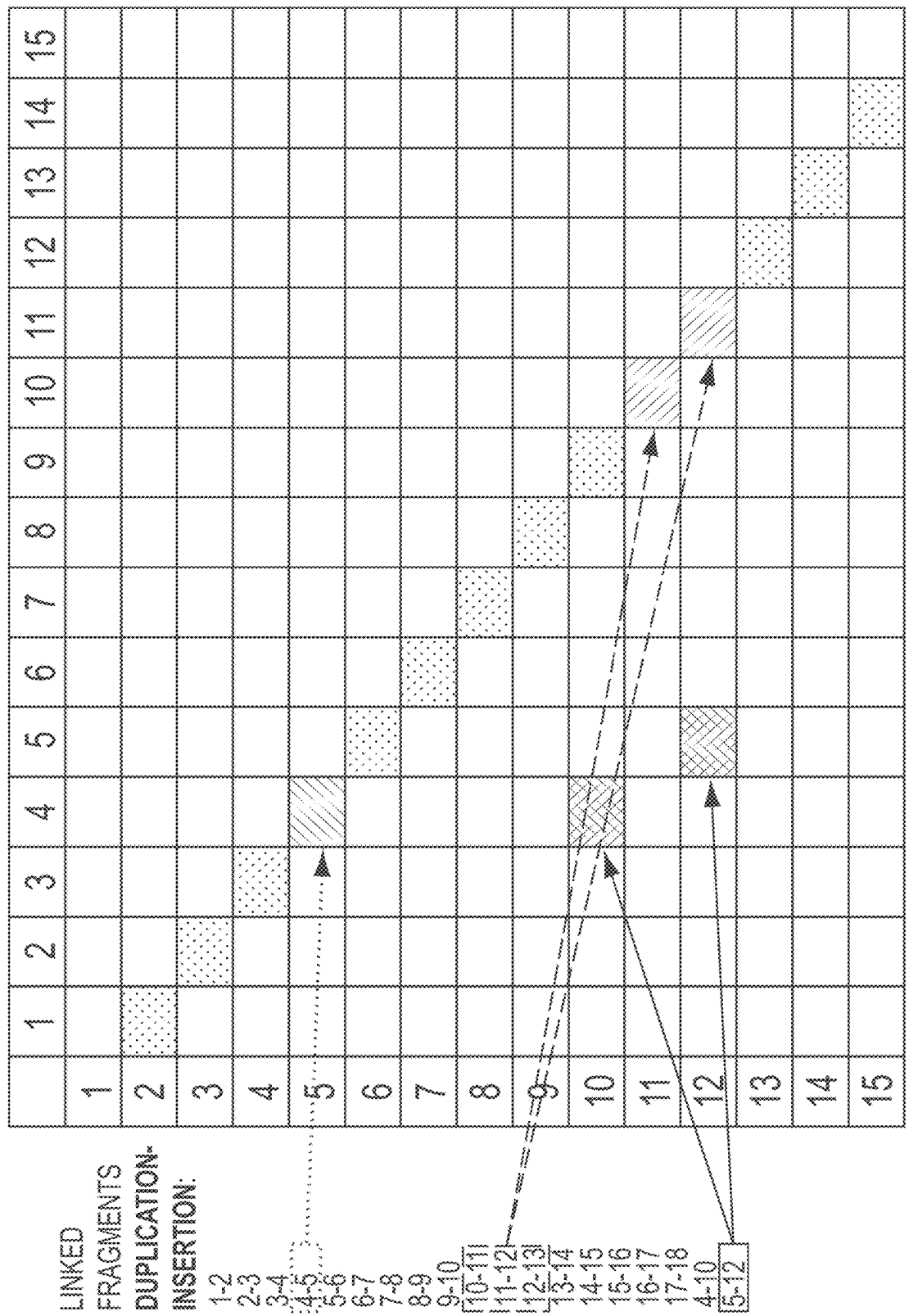
FIG. 5: Contact matrix corresponding to the amplification-insertion of a chromosomal fragment as shown in FIG. 4.

As shown in FIGS. 4 and 5, an amplification and insertion of a fragment within a chromosome can generate two new trans-interaction located at 5' donor and 5' acceptor location and at 3' donor and 3' acceptor location that reveal the length and orientation of the duplication. All cis-interactions within the duplicated fragment are duplicated, and quantification thereof reveals fold amplification of duplication. One single cis-interaction at insertion location is lost which reveals insertion location.

Accordingly, in some embodiments wherein sequencing reads of proximity ligation sequencing are directly used to analyze genome rearrangement and copy number variation, the duplication of a chromosomal fragment can be identified by one or more of: (i) a loss of covalent bonding between a first and second chromosomal fragments that are linked to each other in the reference genome (e.g., loss of contact between 4 and 5 in FIG. 4), (ii) a gain of covalent bonding between the first chromosomal fragment and a third chromosomal fragment, wherein the first chromosomal fragment is separated from the third chromosomal fragment in the reference genome by at least one chromosomal fragment (e.g., gain of contact between 4 and 10 in FIG. 4), (iii) a gain of covalent bonding between the second chromosomal fragment and a fourth chromosomal fragment, wherein the second chromosomal fragment is separated from the fourth chromosomal fragment in the reference genome by at least one chromosomal fragment (e.g., gain of contact between 5 and 12 in FIG. 4), and (iv) an enhancement of covalent bonding between two or more continuous chromosomal fragments, from the third chromosomal fragment to the fourth chromosomal fragment, that are linked to each other in the reference genome (e.g., enhanced contact between 10 and 11 and 11 and 12 in FIG. 4).

In some embodiments, the duplication of a chromosomal fragment can be identified by one or more of: (i) a loss of covalent bonding between a first and second chromosomal fragments that are linked to each other in the reference genome, (ii) a gain of covalent bonding between the first chromosomal fragment and a third chromosomal fragment, wherein the first chromosomal fragment is separated from the third chromosomal fragment in the reference genome by at least one chromosomal fragment, (iii) a gain of covalent bonding between the second chromosomal fragment and the third chromosomal fragment, wherein the second chromosomal fragment is separated from the third chromosomal fragment in the reference genome by at least one chromosomal fragment.

In other embodiments wherein a contact matrix is plotted from proximity ligation sequencing data and used to analyze genome rearrangement and copy number variation, the duplication of a chromosomal fragment can be identified by one or more of: (i) a loss of a cis interaction between a first and second chromosomal fragments that are linked to each other in the reference genome (e.g., loss of contact between 4 and 5 in FIG. 5), (ii) a gain of a trans interaction between the first chromosomal fragment and a third chromosomal fragment, wherein the first chromosomal fragment is separated from the third chromosomal fragment in the reference genome by at least one chromosomal fragment (e.g., gain of contact between 4 and 10 in FIG. 5), (iii) a gain of a trans interaction between the second chromosomal fragment and a fourth chromosomal fragment, wherein the second chromosomal fragment is separated from the fourth chromosomal fragment in the reference genome by at least one chromosomal fragment (e.g., gain of contact between 5 and 12 in FIG. 5), and (iv) an enhancement of one or more cis interactions between two or more continuous chromosomal fragments, from the third chromosomal fragment to the fourth chromosomal fragment, that are linked to each other in the reference genome (e.g., enhanced contact between 10 and 11 and 11 and 12 in FIG. 5).

In other embodiments, the duplication of a chromosomal fragment can be identified by one or more of: (i) a loss of a cis interaction between a first and second chromosomal fragments that are linked to each other in the reference genome, (ii) a gain of a trans interaction between the first chromosomal fragment and a third chromosomal fragment, wherein the first chromosomal fragment is separated from the third chromosomal fragment in the reference genome by at least one chromosomal fragment, (iii) a gain of a trans interaction between the second chromosomal fragment and the third chromosomal fragment, wherein the second chromosomal fragment is separated from the third chromosomal fragment in the reference genome by at least one chromosomal fragment.

Relocation of Chromosomal Fragments within a Genome

In some embodiments, the method described herein can be used to detect relocation of chromosomal fragments.

Figure 6:
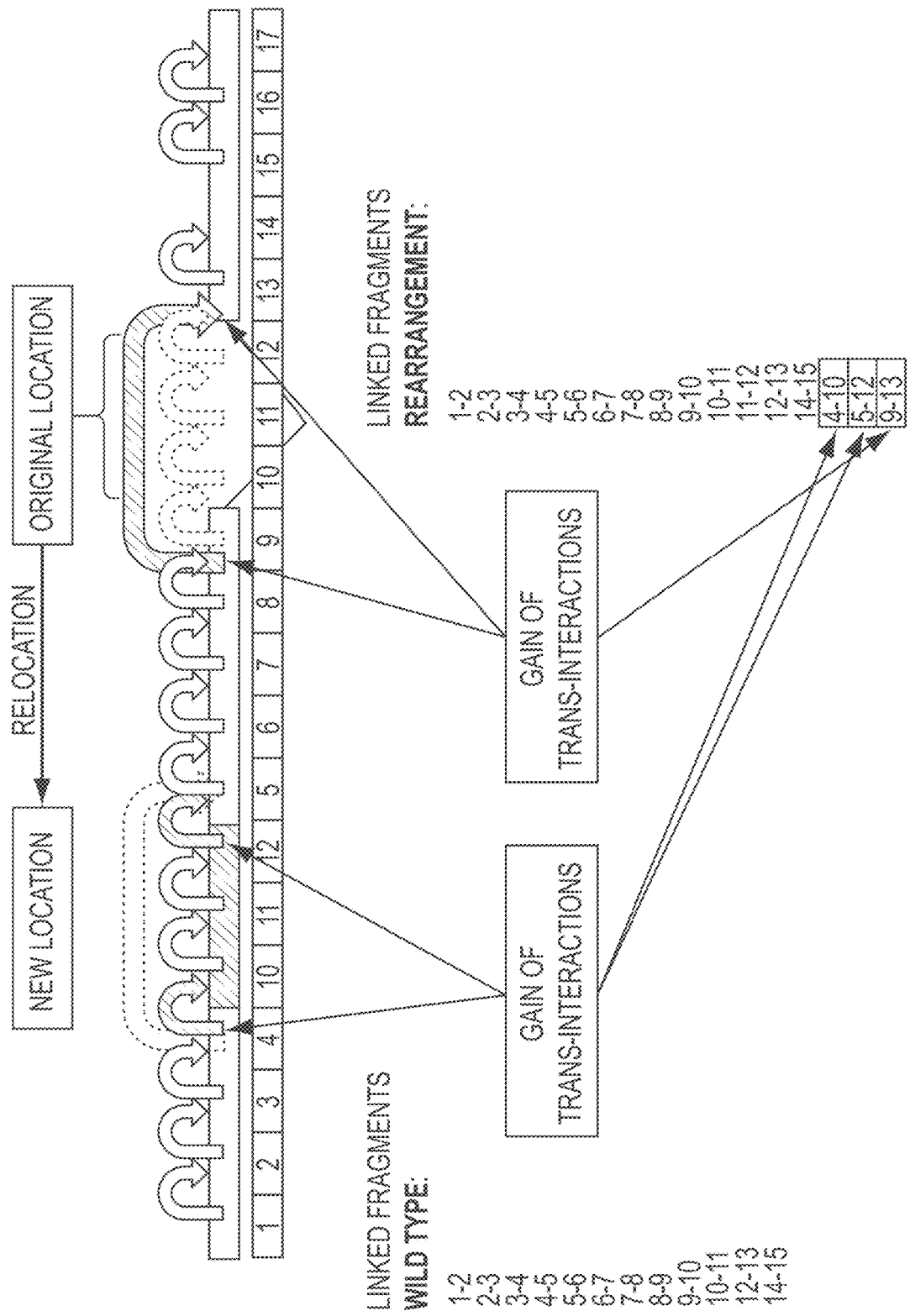
FIG. 6: Relocation of a fragment within a chromosome. A relocation generates multiple changes in a contact matrix, including two new trans-interactions at 5' donor and 5' acceptor location and at 3' donor and 3' acceptor location reveal acceptor location, length and orientation of the insert, as well as one new trans-interaction at reconnection of donor 5' and 3' end reveals donor location and length. Chromosome sequences are divided into consecutively numbered blocks. Block arrows indicate cis- and trans-interactions between sequences blocks, represented by numbered blocks. Lists show linked fragments as block numbers for both interacting sequences separated by a dash. Shown are lists for linked fragments of a wild type chromosome as reference and for the corresponding rearranged chromosome. Thin arrows point at interactions that appear or disappear due to genome rearrangements of various kinds, and connect to the corresponding linked fragments.
Figure 7:
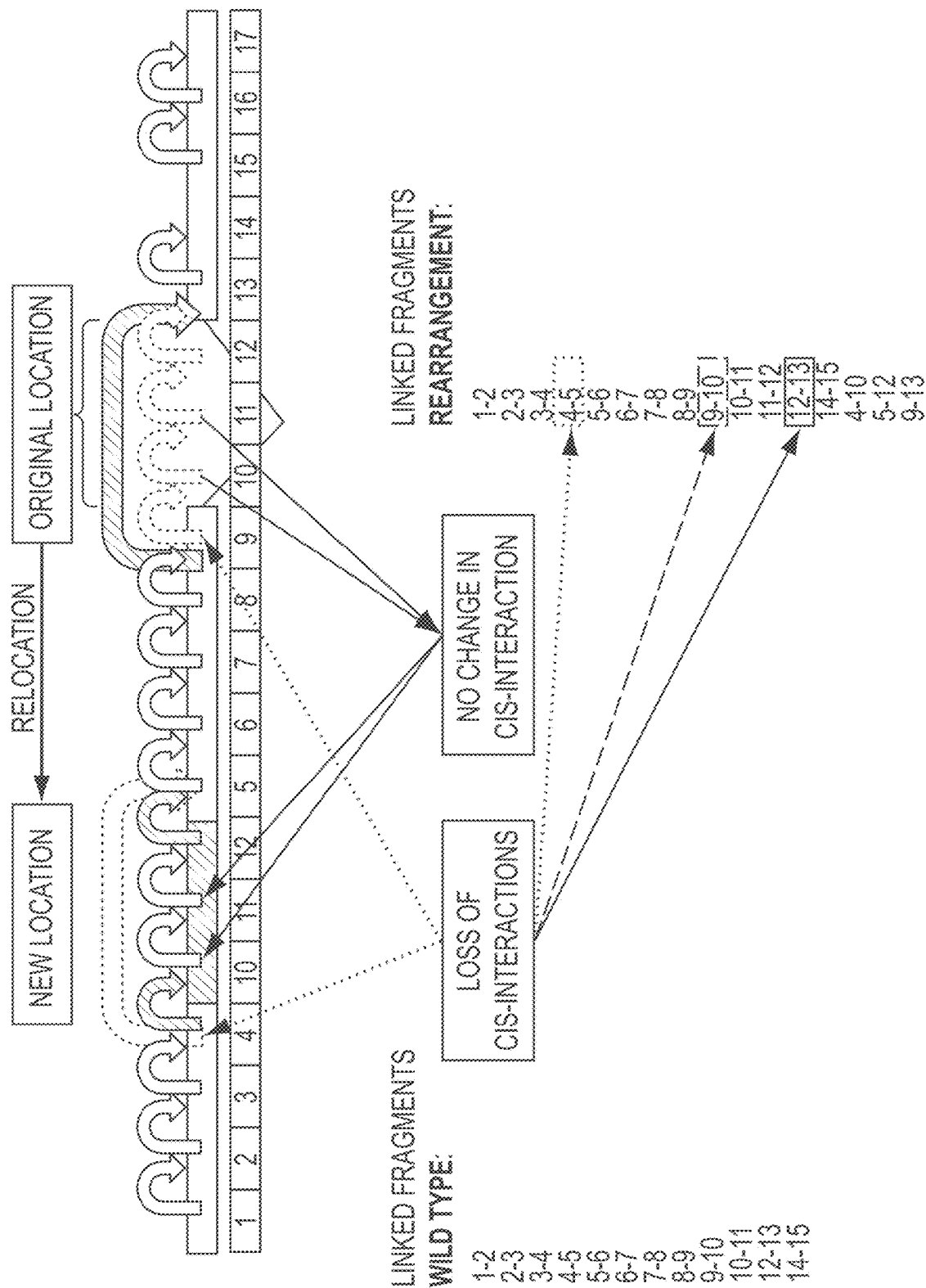
FIG. 7: Relocation of a fragment within a chromosome. One single cis-interaction at insertion location is lost that reveals the acceptor location. Two cis-interactions at the deletion borders are lost which reveals donor location. Chromosome sequences are divided into consecutively numbered blocks. Block arrows indicate cis- and trans-interactions between sequences blocks, represented by numbered blocks. Lists show linked fragments as block numbers for both interacting sequences separated by a dash. Shown are lists for linked fragments of a wild type chromosome as reference and for the corresponding rearranged chromosome. Thin arrows point at interactions that appear or disappear due to genome rearrangements of various kinds, and connect to the corresponding linked fragments.

As shown in FIG. 6, a relocation of a fragment within a chromosome can generate multiple changes in a contact matrix, including two new trans-interactions at 5' donor and 5' acceptor location and at 3' donor and 3' acceptor location which reveal acceptor location, length and orientation of the insert, as well as one new trans-interaction at reconnection of donor 5' and 3' end which reveals donor location and length. In addition, as shown in FIG. 7, one single cis-interaction at insertion location is lost which reveals the acceptor location. Two cis-interactions at the deletion borders are lost which reveals donor location.

Accordingly, in some embodiments wherein sequencing reads of proximity ligation sequencing are directly used to analyze genome rearrangement and copy number variation, the relocation of a chromosomal fragment can be identified by one or more of: (i) a loss of covalent bonding between a first and second chromosomal fragments that are linked to each other in the reference genome (e.g., loss of contact between 4 and 5 in FIG. 7), (ii) a gain of covalent bonding between the first chromosomal fragment and a third chromosomal fragment, wherein the first chromosomal fragment is separated from the third chromosomal fragment in the reference genome by at least one chromosomal fragment (e.g., gain of contact between 4 and 10 in FIG. 6), (iii) a gain of covalent bonding between the second chromosomal fragment and a fourth chromosomal fragment, wherein the second chromosomal fragment is separated from the fourth chromosomal fragment in the reference genome by at least one chromosomal fragment (e.g., gain of contact between 5 and 12 in FIG. 6), (iv) a loss of covalent bonding between the third chromosomal fragment and a fifth chromosomal fragments, wherein the third and fifth chromosomal fragments are linked to each other in the reference genome (e.g., loss of contact between 10 and 9 in FIG. 7), (v) a loss of covalent bonding between the fourth chromosomal fragment and a sixth chromosomal fragments, wherein the fourth and sixth chromosomal fragments are linked to each other in the reference genome (e.g., loss of contact between 12 and 13 in FIG. 7), and (vi) a gain of covalent bonding between the fifth and sixth chromosomal fragments, wherein the fifth chromosomal fragment is separated from the sixth chromosomal fragment in the reference genome by two or more continuous chromosomal fragments, from the third chromosomal fragment to the fourth chromosomal fragment (e.g., gain of contact between 9 and 13 in FIG. 6).

In some embodiments, the relocation of a chromosomal fragment can be identified by one or more of: (i) a loss of covalent bonding between a first and second chromosomal fragments that are linked to each other in the reference genome, (ii) a gain of covalent bonding between the first chromosomal fragment and a third chromosomal fragment, wherein the first chromosomal fragment is separated from the third chromosomal fragment in the reference genome by at least one chromosomal fragment, (iii) a gain of covalent bonding between the second chromosomal fragment and the third chromosomal fragment, wherein the second chromosomal fragment is separated from the third chromosomal fragment in the reference genome by at least one chromosomal fragment, (iv) a loss of covalent bonding between the third chromosomal fragment and a fifth chromosomal fragments, wherein the third and fifth chromosomal fragments are linked to each other in the reference genome, (v) a loss of covalent bonding between the third chromosomal fragment and a sixth chromosomal fragments, wherein the third and sixth chromosomal fragments are linked to each other in the reference genome, and (vi) a gain of covalent bonding between the fifth and sixth chromosomal fragments, wherein the fifth chromosomal fragment is separated from the sixth chromosomal fragment in the reference genome by the third chromosomal fragment.

Figure 8:
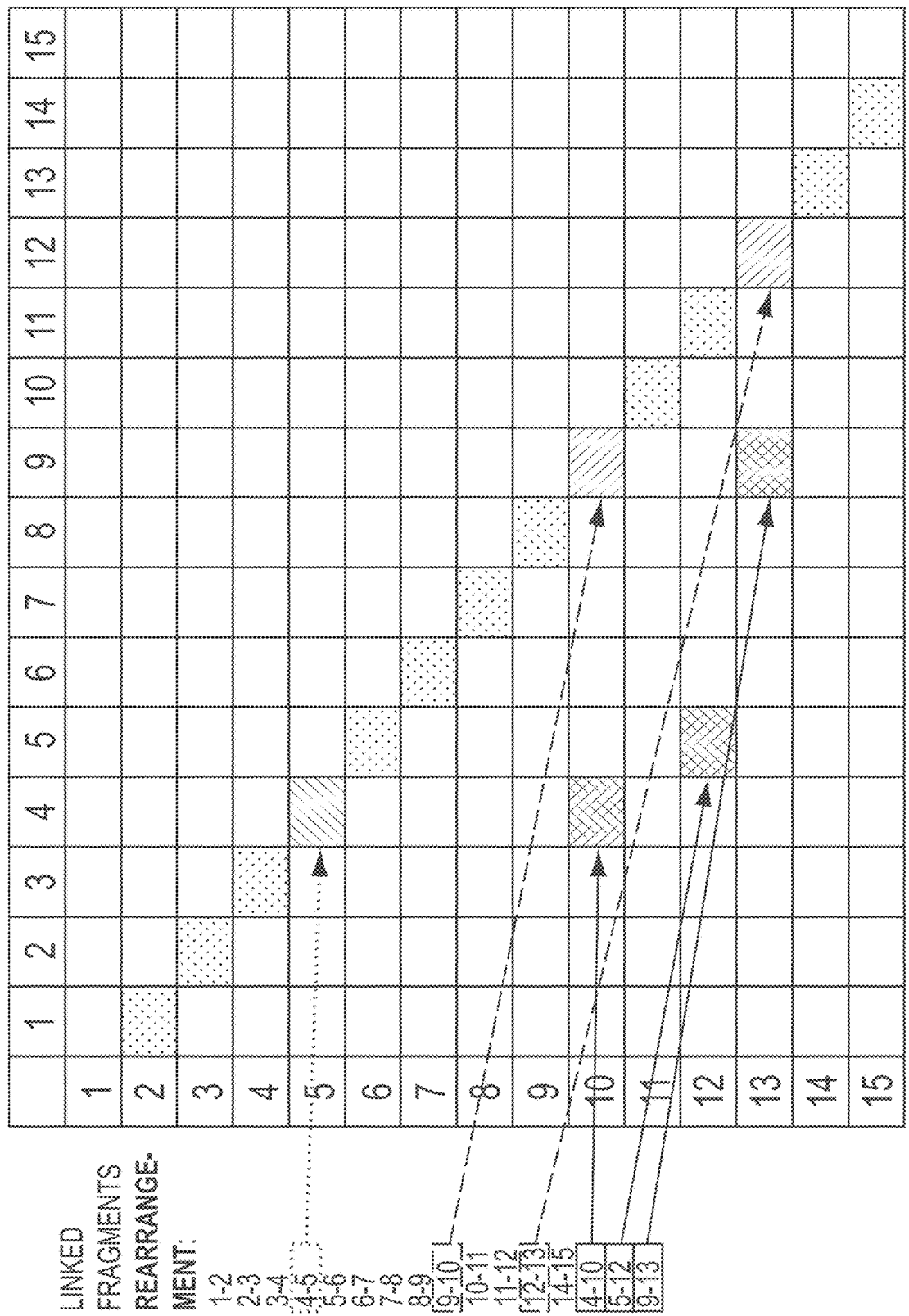
FIG. 8: Contact matrix corresponding to the relocation of a chromosomal fragment as shown in FIGS. 6 and 7.

In other embodiments wherein a contact matrix is plotted from proximity ligation sequencing data and used to analyze genome rearrangement and copy number variation, the relocation of a chromosomal fragment can be identified by one or more of: (i) a loss of a cis interaction between a first and second chromosomal fragments that are linked to each other in the reference genome (e.g., loss of contact between 4 and 5 in FIG. 8), (ii) a gain of a trans interaction between the first chromosomal fragment and a third chromosomal fragment, wherein the first chromosomal fragment is separated from the third chromosomal fragment in the reference genome by at least one chromosomal fragment (e.g., gain of contact between 4 and 10 in FIG. 8), (iii) a gain of a trans interaction between the second chromosomal fragment and a fourth chromosomal fragment, wherein the second chromosomal fragment is separated from the fourth chromosomal fragment in the reference genome by at least one chromosomal fragment (e.g., gain of contact between 5 and 12 in FIG. 8), (iv) a loss of a cis interaction between the third chromosomal fragment and a fifth chromosomal fragments, wherein the third and fifth chromosomal fragments are linked to each other in the reference genome (e.g., loss of contact between 10 and 9 in FIG. 8), (v) a loss of a cis interaction between the fourth chromosomal fragment and a sixth chromosomal fragments, wherein the fourth and sixth chromosomal fragments are linked to each other in the reference genome (e.g., loss of contact between 12 and 13 in FIG. 8), and (vi) a gain of a trans interaction between the fifth and sixth chromosomal fragments, wherein the fifth chromosomal fragment is separated from the sixth chromosomal fragment in the reference genome by two or more continuous chromosomal fragments, from the third chromosomal fragment to the fourth chromosomal fragment (e.g., gain of contact between 9 and 13 in FIG. 8).

In other embodiments, the relocation of a chromosomal fragment can be identified by one or more of: (i) a loss of a cis interaction between a first and second chromosomal fragments that are linked to each other in the reference genome, (ii) a gain of a trans interaction between the first chromosomal fragment and a third chromosomal fragment, wherein the first chromosomal fragment is separated from the third chromosomal fragment in the reference genome by at least one chromosomal fragment, (iii) a gain of a trans interaction between the second chromosomal fragment and the third chromosomal fragment, wherein the second chromosomal fragment is separated from the third chromosomal fragment in the reference genome by at least one chromosomal fragment, (iv) a loss of a cis interaction between the third chromosomal fragment and a fifth chromosomal fragments, wherein the third and fifth chromosomal fragments are linked to each other in the reference genome, (v) a loss of a cis interaction between the third chromosomal fragment and a sixth chromosomal fragments, wherein the third and sixth chromosomal fragments are linked to each other in the reference genome, and (vi) a gain of a trans interaction between the fifth and sixth chromosomal fragments, wherein the fifth chromosomal fragment is separated from the sixth chromosomal fragment in the reference genome by the third chromosomal fragment.

Applications

For diseases and genetic disorders known to be associated with certain copy number variation such as deletion, duplication, or relocation of a chromosomal fragment, the method described herein can also be used for diagnosing the diseases and genetic disorders.

In some embodiment, the invention provides for a method for diagnosing a disease or genetic disorder associated with copy number variation, comprising: subjecting a tissue biopsy sample of a patient to proximity ligation sequencing to obtain proximity ligation sequencing data of at least one chromosome of the tissue biopsy sample; selecting linked chromosomal fragments from the proximity ligation sequencing data, wherein the selected linked chromosomal fragments substantially originate from covalent bonding of two chromosomal fragments; identifying an abnormal covalent bonding pattern of the linked chromosomal fragments compared to a reference genome; comparing the abnormal covalent bonding pattern to one or more known patterns associated with copy number variation to identify a type of copy number variation causing the abnormal covalent bonding pattern and the location and/or length of the copy number variation, wherein the copy number variation identified is correlated to a disease or genetic disorder.

In some embodiment, the invention provides for a method for diagnosing a disease or genetic disorder associated with copy number variation, comprising: subjecting a tissue biopsy sample of patient to proximity ligation sequencing to obtain proximity ligation sequencing data of at least one chromosome of the tissue biopsy sample; obtaining a contact matrix plotted from the proximity ligation sequencing data; identifying an abnormal contact pattern in the contact matrix compared to the contact matrix of a reference genome; and comparing the abnormal contact pattern in the contact matrix to one or more known patterns associated with copy number variation to identify a type of copy number variation causing the abnormal contact pattern and the location and/or length of the copy number variation, wherein the copy number variation identified is correlated to a disease or genetic disorder.

In addition, the method described herein can be used for identifying one or more copy number variations associated with a certain disease or genetic disorder.

In some embodiment, the invention provides for a method for identifying one or more copy number variations causing a disease or genetic disorder, comprising: subjecting a plurality of tissue biopsy samples from patient suffering from a certain disease or genetic disorder to proximity ligation sequencing to obtain proximity ligation sequencing data of at least one chromosome of the tissue biopsy sample; selecting linked chromosomal fragments from the proximity ligation sequencing data, wherein the selected linked chromosomal fragments substantially originate from covalent bonding of two chromosomal fragments; identifying an abnormal covalent bonding pattern of the linked chromosomal fragments compared to a reference genome; comparing the abnormal covalent bonding pattern to one or more known patterns associated with copy number variation to identify a type of copy number variation causing the abnormal covalent bonding pattern and the location and/or length of the copy number variation; and identifying at least one copy number variation common to a statistically significant number of patients suffering from the same disease or genetic disorder.

In some embodiment, the invention provides for a method for identifying one or more copy number variations causing a disease or genetic disorder, comprising: subjecting a plurality of tissue biopsy samples from patient suffering from a certain disease or genetic disorder to proximity ligation sequencing to obtain proximity ligation sequencing data of at least one chromosome of the tissue biopsy sample; obtaining a contact matrix plotted from proximity ligation sequencing data; identifying an abnormal contact pattern in the contact matrix compared to the contact matrix of a reference genome; and comparing the abnormal contact pattern in the contact matrix to one or more known patterns associated with copy number variation to identify a type of copy number variation causing the abnormal contact pattern and the location and/or length of the copy number variation; and identifying at least one copy number variation common to a statistically significant number of patients suffering from the same disease or genetic disorder.

Further Implementations

Many embodiments disclosed herein may be implemented in digital electronic circuitry, integrated circuitry, specially designed ASICs (application-specific integrated circuits), computer hardware, firmware, software, or in combinations thereof. Method steps of the presently disclosed embodiments can be performed by a programmable processor executing a program of instructions to perform functions of the presently disclosed embodiments by operating on input data and generating output; and apparatus relating to the presently disclosed embodiments can be implemented in a computer program product tangibly embodied in a machine-readable storage device for execution by a programmable processor. The presently disclosed embodiments can be implemented advantageously in one or more computer programs that are executable and/or interpretable on a programmable system including at least one programmable processor, which may be special or general purpose, coupled to receive data and instructions from, and to transmit data and instructions to, a storage system, at least one input device, and at least one output device. Each computer program can be implemented in a high-level procedural or object-oriented programming language or in assembly or machine language if desired; and in any case, the language can be a compiled or interpreted language. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes any type of non-transitory computer readable medium including, but not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Any of the methods described herein may include the output of data in a physical format, such as on a computer screen, or on a paper printout. In explanations of any embodiments elsewhere in this document, it should be understood that the described methods may be combined with the output of the actionable data in a format that can be acted upon by a physician. In addition, the described methods may be combined with the actual execution of a clinical decision that results in a clinical treatment, or the execution of a clinical decision to make no action. Some of the embodiments described herein may be combined with the output of the actionable data, and the execution of a clinical decision that results in a clinical treatment, or the execution of a clinical decision to make no action.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A method for detecting genome rearrangement in a biological sample, comprising:
    subjecting the biological sample to proximity ligation sequencing to obtain proximity ligation sequencing data of at least one chromosome of the biological sample;
    obtaining a contact matrix plotted from the proximity ligation sequencing data of at least one chromosome of the biological sample, wherein the contact matrix comprises locations of contacts and contact frequencies between linked chromosomal fragments, wherein linked chromosomal fragments originating from non-covalent interactions are separated from linked chromosomal fragments originating from covalent bonding based on the contact frequencies to determine a covalent contact pattern in the contact matrix;
    identifying an abnormal covalent contact pattern in the contact matrix compared to the contact matrix of a reference genome; and
    comparing the abnormal covalent contact pattern in the contact matrix to one or more known patterns associated with genomic rearrangement to identify a type of genomic rearrangement causing the abnormal contact pattern.

2. The method of claim 1, wherein the genomic rearrangement identified is deletion of chromosomal fragments.

3. The method of claim 2, wherein the deletion of a chromosomal fragment is identified by:
    (i) a loss of one or more cis interactions between two or more continuous chromosomal fragments that are linked to each other in the reference genome, and
    (ii) a gain of a trans interaction between two chromosomal fragments that are separated by the two or more continuous chromosomal fragments in the reference genome.

4. The method of claim 1, wherein the genomic rearrangement identified is duplication of chromosomal fragments.

5. The method of claim 4, wherein the duplication of a chromosomal fragment is identified by:

(i) a loss of a cis interaction between a first and second chromosomal fragments that are linked to each other in the reference genome, (ii) a gain of a trans interaction between the first chromosomal fragment and a third chromosomal fragment, wherein the first chromosomal fragment is separated from the third chromosomal fragment in the reference genome by at least one chromosomal fragment;

(iii) a gain of a trans interaction between the second chromosomal fragment and a fourth chromosomal fragment, wherein the second chromosomal fragment is separated from the fourth chromosomal fragment in the reference genome by at least one chromosomal fragment; and (iv) an enhancement of one or more cis interactions between two or more continuous chromosomal fragments, from the third chromosomal fragment to the fourth chromosomal fragment, that are linked to each other in the reference genome.

6. The method of claim 1, wherein the genomic rearrangement identified is relocation of chromosomal fragments.

7. The method of claim 6, wherein the relocation of chromosomal fragments is identified by:

(i) a loss of a cis interaction between a first and second chromosomal fragments that are linked to each other in the reference genome, (ii) a gain of a trans interaction between the first chromosomal fragment and a third chromosomal fragment, wherein the first chromosomal fragment is separated from the third chromosomal fragment in the reference genome by at least one chromosomal fragment;

(iii) a gain of a trans interaction between the second chromosomal fragment and a fourth chromosomal fragment, wherein the second chromosomal fragment is separated from the fourth chromosomal fragment in the reference genome by at least one chromosomal fragment;

(iv) a loss of a cis interaction between the third chromosomal fragment and a fifth chromosomal fragments, wherein the third and fifth chromosomal fragments are linked to each other in the reference genome;

(v) a loss of a cis interaction between the fourth chromosomal fragment and a sixth chromosomal fragments, wherein the fourth and sixth chromosomal fragments are linked to each other in the reference genome; and (vi) a gain of a trans interaction between the fifth and sixth chromosomal fragments, wherein the fifth chromosomal fragment is separated from the sixth chromosomal fragment in the reference genome by two or more continuous chromosomal fragments, from the third chromosomal fragment to the fourth chromosomal fragment.

8. A method for diagnosing a disease or genetic disorder associated with copy number variation, comprising:

subjecting a tissue biopsy sample of a patient to proximity ligation sequencing to obtain proximity ligation sequencing data of at least one chromosome of the tissue biopsy sample;

selecting linked chromosomal fragments from the proximity ligation sequencing data, wherein the selected linked chromosomal fragments substantially originate from covalent bonding of two chromosomal fragments;

identifying an abnormal covalent bonding pattern of the linked chromosomal fragments compared to a reference genome;

comparing the abnormal covalent bonding pattern to one or more known patterns associated with copy number variation to identify a type of copy number variation causing the abnormal covalent bonding pattern and the location and/or length of the copy number variation, wherein the copy number variation identified is correlated to a disease or genetic disorder.

9. A method for diagnosing a disease or genetic disorder associated with copy number variation, comprising:

subjecting a tissue biopsy sample of patient to proximity ligation sequencing to obtain proximity ligation sequencing data of at least one chromosome of the tissue biopsy sample;

obtaining a contact matrix plotted from the proximity ligation sequencing data, wherein the contact matrix comprises locations of contacts and contact frequencies between linked chromosomal fragments, wherein linked chromosomal fragments originating from non-covalent interactions are separated from linked chromosomal fragments originating from covalent bonding based on the contact frequencies to determine a covalent contact pattern in the contact matrix;

identifying an abnormal covalent contact pattern in the contact matrix compared to the contact matrix of a reference genome; and comparing the abnormal covalent contact pattern in the contact matrix to one or more known patterns associated with copy number variation to identify a type of copy number variation causing the abnormal contact pattern and the location and/or length of the copy number variation, wherein the copy number variation identified is correlated to a disease or genetic disorder.

10. The method of claim 1, wherein the proximity ligation sequencing comprises crosslinking genomic DNAs in situ, digesting the crosslinked DNA with at least one restriction enzyme to obtain digested DNA, ligating the digested DNA to obtain linked fragments, and sequencing the linked fragments to obtain the proximity ligation sequencing data; and wherein the proximity ligation sequencing data of a chromosome are plotted into the contact matrix showing both locations of contacts and contact frequencies thereof.

11. The method of claim 1, wherein the biological sample is a human tissue biopsy sample.

12. The method of claim 1, further comprising identifying the location, length, and/or orientation of the genome arrangement.

13. The method of claim 8, wherein the proximity ligation sequencing comprises crosslinking genomic DNAs in situ, digesting the crosslinked DNA with at least one restriction enzyme to obtain digested DNA, ligating the digested DNA to obtain linked fragments, and sequencing the linked fragments to obtain the proximity ligation sequencing data.

14. The method of claim 8, wherein the biological sample is a human tissue biopsy sample.

15. The method of claim 8, further comprising identifying the location, length, and/or orientation of the genome arrangement.

16. The method of claim 9, wherein the proximity ligation sequencing comprises crosslinking genomic DNAs in situ, digesting the crosslinked DNA with at least one restriction enzyme to obtain digested DNA, ligating the digested DNA to obtain linked fragments, and sequencing the linked fragments to obtain the proximity ligation sequencing data; and wherein the proximity ligation sequencing data of a chromosome are plotted into the contact matrix showing both locations of contacts and contact frequencies thereof.

17. The method of claim 9, wherein the biological sample is a human tissue biopsy sample.

18. The method of claim 9, further comprising identifying the location, length, and/or orientation of the genome arrangement.

\* \* \* \* \*